United States Patent
Worley

(10) Patent No.: US 8,100,127 B2
(45) Date of Patent: Jan. 24, 2012

(54) CATHETER GUIDING FLEXIBLE CONNECTOR

(76) Inventor: Brian D. Worley, Tulsa, OK (US)

( * ) Notice: Subject to any disclaimer, the term of this patent is extended or adjusted under 35 U.S.C. 154(b) by 619 days.

(21) Appl. No.: 11/998,289

(22) Filed: Nov. 29, 2007

(65) Prior Publication Data

US 2009/0139529 A1    Jun. 4, 2009

(51) Int. Cl.
  *A62B 9/04* (2006.01)
  *A61M 16/00* (2006.01)
  *A62B 9/06* (2006.01)
(52) U.S. Cl. ............... 128/207.14; 128/202.27
(58) Field of Classification Search ............ 128/202.27, 128/207.14–207.18; 604/533, 514, 19, 921
See application file for complete search history.

(56) References Cited

U.S. PATENT DOCUMENTS

| | | | |
|---|---|---|---|
| 3,991,762 A | 11/1976 | Radford | |
| 4,838,258 A * | 6/1989 | Dryden et al. | 128/204.18 |
| 4,852,564 A * | 8/1989 | Sheridan et al. | 128/202.27 |
| 4,995,872 A | 2/1991 | Ferrara | |
| 7,059,322 B2 * | 6/2006 | Rich et al. | 128/200.24 |
| 2002/0143301 A1 * | 10/2002 | Lopez | 604/256 |
| 2007/0181130 A1 | 8/2007 | Worley | |
| 2007/0181132 A1 | 8/2007 | Worley | |

FOREIGN PATENT DOCUMENTS

DE    296 04 185 U1    4/1996

OTHER PUBLICATIONS

International Search Report and Written Opinion issued Feb. 12, 2009 by the International Searching Authority (ISA/US) in corresponding PCT/US08/13068; 8 pages.
International Preliminary Report on Patentability issued by the International Bureau on Jun. 10, 2010 in PCT/US2008/013068 (5 pgs).
Levent Turkavci, "Supplementary European Search Report," EP 08 85 5013, European Patent Office (Munich), (Nov. 26, 2010).

* cited by examiner

*Primary Examiner* — Matthew F Desanto
(74) *Attorney, Agent, or Firm* — Gable Gotwals

(57) ABSTRACT

A flexible connector couples the inlet end of a tracheotomy tube inner cannula to an outlet port of an in-line catheter. The catheter exit end of the connector is adapted to be serially coupled in pneumatic communication with the inlet end of the tracheotomy tube inner cannula and also to guide the downstream tip of the catheter into the inlet end of the inner cannula in response to pushing of the catheter upstream of the catheter outlet port. Thus, the in-line catheter can be inserted into the tracheotomy tube inner cannula with little likelihood of having to compress or "flip" the connector or disconnect the connector from the tracheotomy tube and the patient from the ventilator circuit.

6 Claims, 3 Drawing Sheets

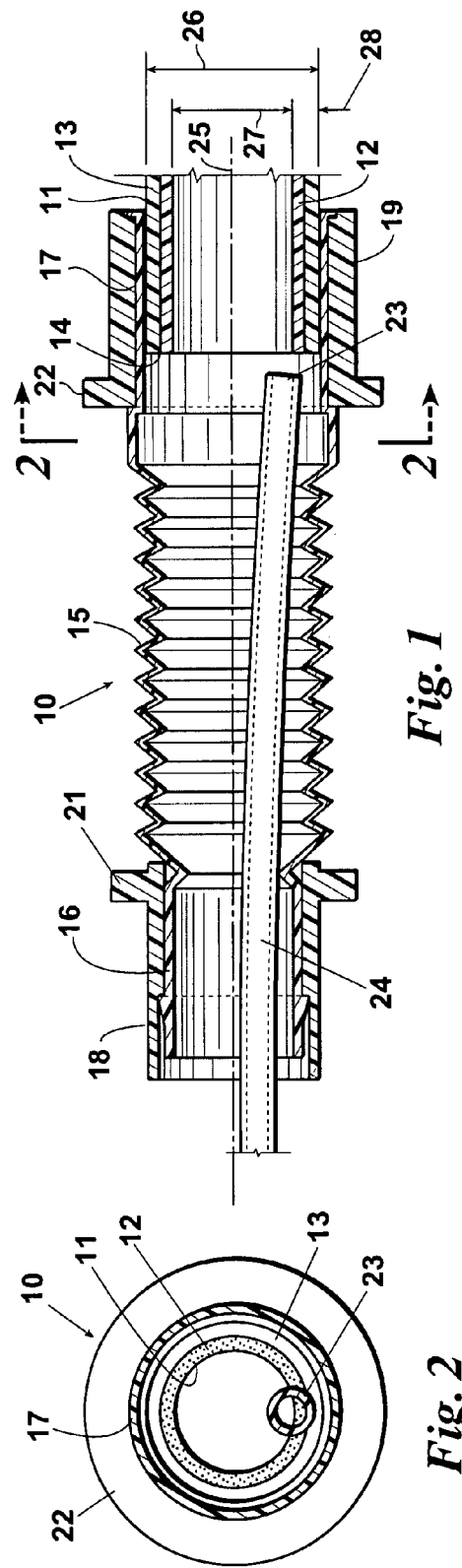
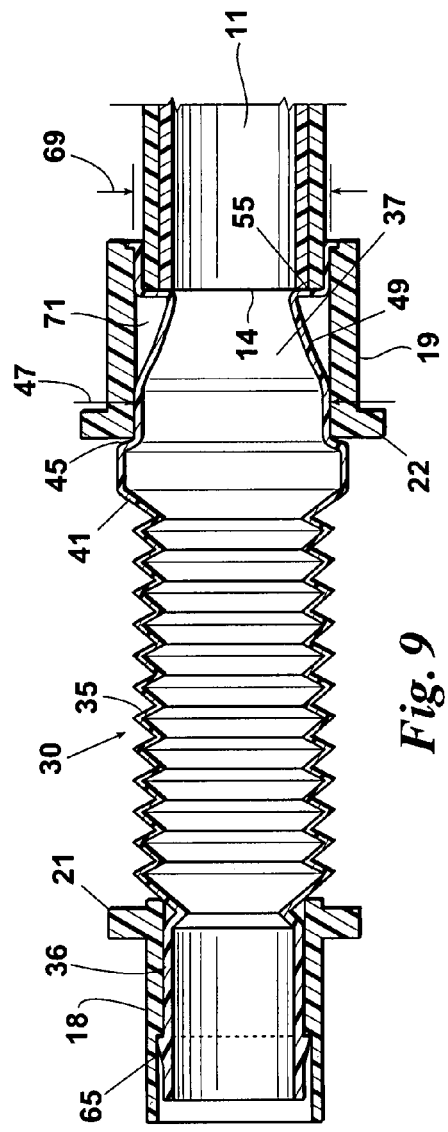
Fig. 1 (PRIOR ART)
Fig. 2 (PRIOR ART)
Fig. 9

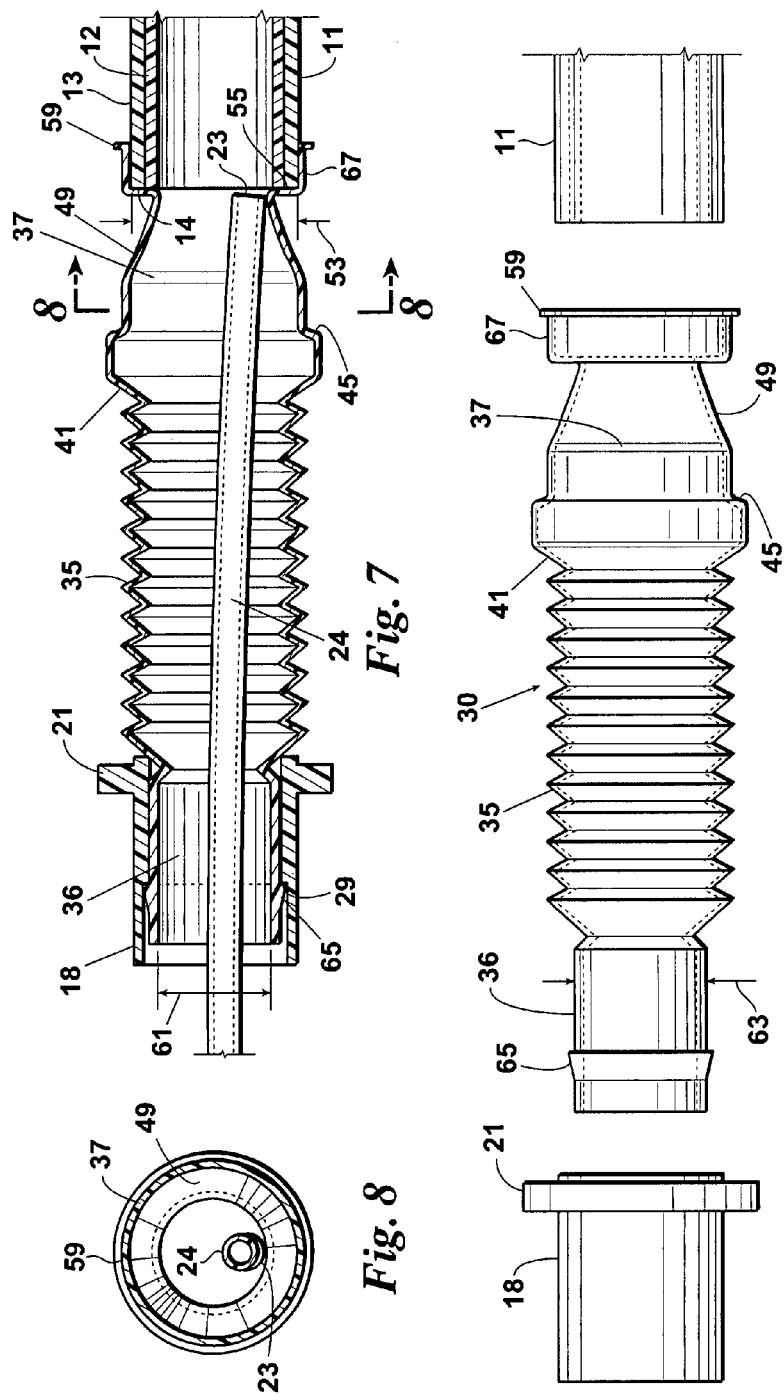

CATHETER GUIDING FLEXIBLE CONNECTOR

BACKGROUND OF THE INVENTION

This invention relates generally to tracheotomy associated equipment and more particularly concerns flexible connectors for coupling in-line catheters to tracheotomy tube inner cannulas.

In-line suction catheters are used to permit a patient to continuously respirate through a tracheotomy tube while the catheter is inserted into the inner cannula of the tracheotomy tube. The in-line catheter has a housing with two inlet ports and an outlet port. A ventilator circuit is connected to one of the housing inlet ports. The catheter extends into the housing through the other housing inlet port. A flexible connector couples the housing outlet port in serial communication with the inlet or ventilator end of the inner cannula. The air and catheter are pushed through the flexible connector into the inlet end of the cannula for administration to the patient. The flexible connector consists of an accordion-like tubular body with entry and exit collars on its respective ends taken in relation to the direction of insertion of the catheter. The exit end of the flexible connector slips onto the entry end of the inner cannula and the entry end of the flexible connector slips into the outlet port of the in-line catheter housing.

In-line suction catheters, as they are inserted through known flexible connectors into the entry end of the inner cannula, almost always hang up on the inlet face of the insertion end of the cannula. This interference necessitates immediate implementation of one or more remedial actions until the problem is resolved. Initially, the flexible connector is longitudinally compressed to decrease the length between the tip of the in line suction catheter and the ventilator end of inner cannula. If compression does not resolve the problem, the suction catheter is twisted and turned in an attempt to "flip" it into the entry to the inner cannula. These actions cause discomfort to the patient, lengthen the time required for completion of the procedure, waste the valuable time of respiratory therapists and nurses and expend possibly precious time for the patient undergoing the procedure.

If neither compression nor "flipping" are successful, the inline suction catheter is eventually disconnected from the ventilator circuit. In this case, the procedure is further lengthened by the extra time to needed to disconnect and reassemble the ventilator circuit. More significantly, disconnection causes a loss of ventilator pressure to the patient which can be rapidly physiologically catastrophic, cause a loss of sterility possibly resulting in more infections and further subject the patient to more stressful discomfort including the experience of a "smothering" feeling from no longer being on the ventilator. Furthermore, some patients require the pressure created by the ventilator circuit to keep their airways free of fluid and allow oxygenation/ventilation to occur. Once pressure is lost, the procedure has embarked on down hill course. A disconnect from the pressure of the ventilator circuit can result in rapid "flooding" of the alveoli with fluid, resulting in extremely quick decompensation, perhaps in as little as the time for eight breaths. When the ventilator circuit is reconnected, it can take several hours for the regained pressure to clear the alveoli of fluid. For patients who are dependent on maintenance of continued pressure, it is imperative that no disconnects occur as the benefits of loss of pressure are quickly lost and slowly regained.

In a worst case scenario, once the connector has been removed and the in-line suction catheter has been placed directly on the inner cannula, the catheter may still hang up on the cannula entry face. In this event, it is necessary to acquire from supply and install a different type of suction catheter which can be passed directly into the inner cannula entry, leaving the patient completely off the ventilator and increasing the time and expense of the procedure and the risks and discomfort to the patient.

It is, therefore, an object of this invention to provide a flexible connector which facilitates easy passage of an inline suction catheter into a tracheotomy tube inner cannula. Another object of this invention is to provide a flexible connector which does not require longitudinal compression to accomplish passage of an inline suction catheter into a tracheotomy tube inner cannula. A further object of this invention is to provide a flexible connector which, even when arcuately flexed, will readily pass an inline suction catheter into a tracheotomy tube inner cannula. Yet another object of this invention is to provide a flexible connector which does not require twisting and turning of the suction catheter to "flip" the catheter into the inner cannula. It is also an object of this invention to provide a flexible connector which reduces the likelihood of need to disconnect the patient from the ventilator to accomplish passage of a catheter into a tracheotomy tube inner cannula.

SUMMARY OF THE INVENTION

In accordance with the invention, a flexible connector is provided for coupling the inlet end of a tracheotomy tube inner cannula to an outlet port of an in-line catheter. The connector has an elongated, flexible, accordion-like tubular body. The catheter entry end of the tubular body is adapted to be serially coupled in pneumatic communication with the catheter outlet port. The catheter exit end of the tubular body is adapted to be serially coupled in pneumatic communication with the inlet end of the tracheotomy tube inner cannula and to guide the downstream tip of the catheter into the inlet end of the inner cannula in response to pushing of the catheter upstream of the catheter outlet port.

In a preferred embodiment of the connector, the guiding adaptation is a gradual taper in a downstream direction. The taper has an inner diameter at its upstream end substantially equal to the outer diameter of the inlet end of the inner cannula and an inner diameter at its downstream end not greater than the inner diameter of the inlet end of the inner cannula. A flat wall is provided about the downstream end of the gradual taper. The wall has a thickness substantially equal to the thickness of the entry end face of the inner cannula. A portion of constant diameter extends downstream from the flat wall and cooperates with the flat wall to form a cup for the entry end of the inner cannula. When the inner cannula is inserted into abutment against the flat wall of the cup, the diameter of the downstream passageway of the taper is not greater than the diameter of the passageway into the abutting cannula, so a catheter cannot "hang up" on the cannula.

It is also preferred that the exit end of the connector have a bearing portion with an outer diameter substantially equal to the outer diameter of the cup. The bearing portion extends upstream from the upstream end of the gradual taper. A hard sleeve concentrically disposed about and spanning across the bearing portion and the cup creates a void between the sleeve and the connector, but the bearing portion and cup afford sufficient contact to enable manipulation of the exit end of the connector by manipulation of the hard sleeve. A radial expansion at the upstream end of the bearing portion and an annular rim on the downstream end of the cup cooperate to prevent longitudinal motion of the sleeve on the connector.

BRIEF DESCRIPTION OF THE DRAWINGS

Other objects and advantages of the invention will become apparent upon reading the following detailed description and upon reference to the drawings in which:

FIG. 1 is a longitudinal diametric cross-sectional view of a known flexible connector with a catheter inserted therein;

FIG. 2 is a cross-sectional view taken along the line 2-2 of FIG. 1;

FIG. 6 is a side elevation assembly view of the flexible connector of FIG. 3 with a hard sleeve at the entry end of the connector and the entry end of a tracheotomy tube inner cannula at the exit end of the connector;

FIG. 7 is a longitudinal diametric cross-sectional view of the assembled components of FIG. 6 with a catheter inserted in the flexible connector;

FIG. 8 is a cross-sectional view taken along the line 8-8 of FIG. 7; and

FIG. 9 is a longitudinal diametric cross-sectional view of the assembled components of FIG. 6 with a hard sleeve mounted on the exit end of the connector.

Figure 4:
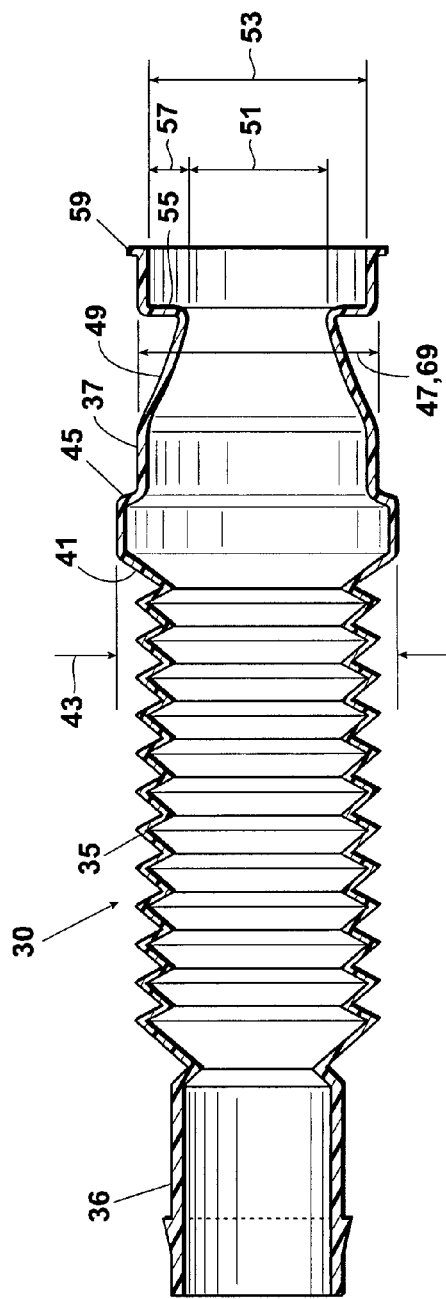
FIG. 4 is a cross-sectional view taken along the line 4-4 of FIG. 3.

While the invention will be described in connection with a preferred embodiment thereof, it will be understood that it is not intended to limit the invention to that embodiment or to the details of the construction or arrangement of parts illustrated in the accompanying drawings.

DETAILED DESCRIPTION

Turning first to FIGS. 1 and 2, a typical known flexible connector 10 is illustrated. The connector 10 is commonly used to couple the inlet end of a tracheotomy tube inner cannula 11 to the outlet port of an in-line catheter (not shown). The cannula 11 has a soft inner liner 12 and a hard outer case 13 which terminate at a relatively thick inlet face 14. The connector 10 has an elongated, flexible, accordion-like tubular body 15. The catheter entry end 16 of the tubular body is adapted to be serially coupled in pneumatic communication with the catheter outlet port (not shown). The catheter exit end 17 of the tubular body 15 is adapted to be serially coupled in pneumatic communication with the inlet end of the tracheotomy tube inner cannula 11. The entry and exit ends 16 and 17 of the connector body 15 are fitted with hard sleeves 18 and 19 with outer annular flanges 21 and 22, respectively. The sleeves 18 and 19 and flanges 21 and 22 are helpful in manipulating the connector 10 which, by reason of its size and configuration and its contact during use with fluids which make its surface extremely slippery, can be quite awkward.

As best seen in FIG. 1, the tip 23 of the catheter 24 has been inserted serially into the entry end 16, body 15 and exit end 17 of the connector 10 until the tip 23 is in close proximity to the inlet face 14 of the inner cannula 11. As shown, even when the connector 10 is perfectly aligned along its longitudinal axis 25, the catheter 24 tends to bow under its own weight so that, as best seen in FIG. 2, the tip 23 at least partially aligns longitudinally with the entry face 14 of the inner cannula 11. Further insertion of the catheter 24 into the connector 10 will cause the tip 23 to "hang up" on the cannula face 14, blocking passage of the catheter 24 into the cannula 11 and initiating the sequence of undesirable events and consequences hereinbefore discussed. Considering that the intended purpose of the design of the connector 15 is to permit it to be stretched, compressed and bent and that the catheter 24 must also be sufficiently flexible to travel a somewhat tortuous path, it is unlikely that the catheter tip 23 will not "hang up" on the cannula face 14, as has been evidenced in practice for many years.

Figure 3:
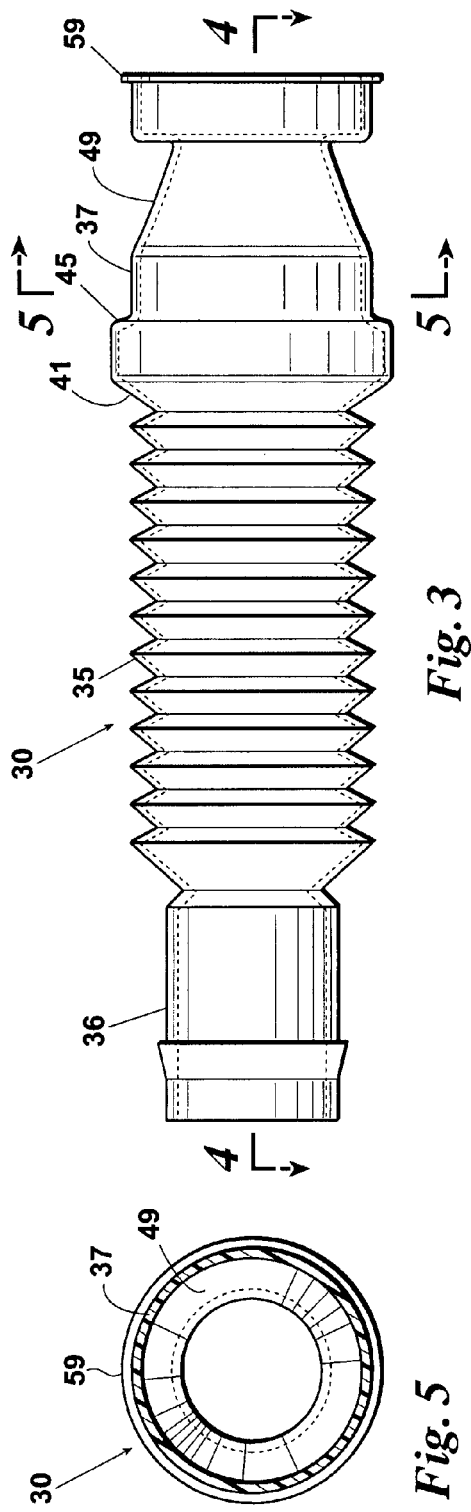
FIG. 3 is a side elevation view of a preferred embodiment of a flexible connector in accordance with the invention.
Figure 5:
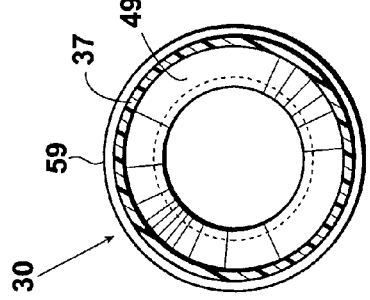
FIG. 5 is a cross-sectional view taken along the line 5-5 of FIG. 3.

Looking now at FIGS. 3-5, a preferred embodiment of a flexible connector 30 according to the invention is illustrated. The new flexible connector 30, like its predecessor connector 10, has an elongated, flexible, accordion-like tubular body 35 with its catheter entry end 36 and its catheter exit end 37 adapted to be serially coupled in pneumatic communication with the catheter outlet port (not shown) and with the inlet end of the tracheotomy tube inner cannula 11 seen in FIGS. 1 and 2, respectively. However, the catheter exit end 37 of the body 35 is modified to guide the downstream tip 23 of the catheter 24 into the inlet end of the inner cannula 11 in response to pushing of the catheter 24 at a point upstream of the catheter outlet port (not shown).

In the preferred embodiment of the connector 30 shown, and following the contour of the catheter exit end 37 of the body 35 in a downstream direction, a taper 41 expands the exit end 37 to a maximum outer diameter 43 greater than outer diameter 26 of the entry end of the inner cannula 11, as seen in FIG. 1. The maximum outer diameter 43 is then contracted to form an annular stop 45 on the outer surface of the exit end 37, the outer diameter 47 of the exit end 37 being substantially equal to the outer diameter 26 of the entry end of the inner cannula 11. The exit end 37 then has a gradual taper 49 to an inner diameter 51 which is substantially equal to the inner diameter 27 of the entry face 14 of the inner cannula 11. The exit end 37 of the connector 30 then radially expands to an inner diameter 53 substantially equal to the outer diameter 26 of the entry end of the inner cannula 11, forming a flat downstream wall 55 of thickness 57 substantially equal to the thickness 28 of the inner cannula entry face 14, as seen in FIG. 1. The exit end 37 of the connector 30 extends downstream from the wall 55 at a constant inner diameter 53 and terminates at an annular rim 59.

Looking at FIGS. 6-8, the entry end 36 of the connector 30 is similar in all respects to the entry end 16 of the known connector 10 seen in FIG. 1. Its inner diameter 61 is sized to receive the downstream end of the outlet port of the catheter housing (not shown). Its outside diameter 63 is sized to be inserted into the entry hard sleeve 18 and an annular stop 65 is positioned on its outer surface to engage an annular seat 29 in the sleeve 18. The seat 29 and stop 65 are positioned to prevent axial motion of the sleeve 18 on the connector 30 when the downstream end of the sleeve 18 abuts the proximal accordion surface of the body 35.

Continuing to look at FIGS. 6-8, the downstream portion of the exit end 37 of the connector 30 defined by the constant inner diameter 53 and the wall 55 form a cup 67 for receiving the entry end of the inner cannula 11. The inner cannula 11 is inserted into the cup 67 until the cannula entry face 14 abuts the connector wall 55. When the catheter 24 is inserted serially into the entry end 36, body 35 and exit end 37 of the connector 30 until the tip 23 is in close proximity to the inlet face 14 of the inner cannula 11, the gradual taper 49 leading up to the cup 67 guides the downstream tip 23 of the catheter 24 into the inlet end of the inner cannula 11 in response to further pushing of the catheter 24 from a position upstream of the catheter outlet port (not shown), as is best seen FIG. 7. Thus, when the cannula face 14 and the connector wall 55 are in abutment, the catheter tip 23 cannot "hang up" on the entry face 14 of the inner cannula 11, as is best seen in FIG. 8. This is true whether the connector 30 is straight, stretched, compressed or bent.

Turning to FIG. 9, the outer diameters 47 and 69 at the stop 45 and of the cup 67, respectively, are substantially equal. Therefore, the hard sleeve 19 can be fitted on these constant diameter portions and used to manipulate the exit end 37 of the connector 30 even though the gradual taper 49 creates an annular void 71 between the connector 30 and the hard sleeve 19.

The connector 30 has been described in relation to an inner cannula 11 of a tracheotomy tube having inner and outer cannulae. Some tracheotomy tubes have a single cannula which, for purposes of using the modified cannula 30, may be considered as the inner cannula herein discussed.

Thus, it is apparent that there has been provided, in accordance with the invention, a flexible connector that fully satisfies the objects, aims and advantages set forth above. While the invention has been described in conjunction with a specific embodiment thereof, it is evident that many alternatives, modifications and variations will be apparent to those skilled in the art and in light of the foregoing description. Accordingly, it is intended to embrace all such alternatives, modifications and variations as fall within the scope of the appended claims.

What is claimed is:

1. For coupling the inlet end of a tracheotomy tube inner cannula to an outlet port of an in-line catheter, a connector comprising:
   an elongated, flexible, accordion-like tubular body;
   means on a catheter entry end of said tubular body for serially coupling said body in pneumatic communication with the catheter outlet port;
   means on a catheter exit end of said tubular body for serially coupling said body in pneumatic communication with the inlet end of the tracheotomy tube inner cannula; and
   a gradual taper on said means on a catheter exit end, said taper having an inner diameter at its upstream end substantially equal to an outer diameter of the inlet end of the inner cannula, an inner diameter at its downstream end not greater than an inner diameter of the inlet end of the inner cannula and a flat wall about a downstream end of said gradual taper, said wall having a thickness substantially equal to a thickness of an entry end face of the inner cannula, whereby a downstream tip of the catheter is guided into the inlet end of the inner cannula in response to pushing the catheter at a location upstream of the catheter outlet port.

2. A connector according to claim 1 further comprising a portion of constant diameter extending downstream from said flat wall and cooperable with said flat wall to form a cup for the entry end of the inner cannula.

3. A connector according to claim 2 further comprising a bearing portion having an outer diameter substantially equal to an outer diameter of said cup extending upstream from said upstream end of said gradual taper.

4. A connector according to claim 3 further comprising a hard sleeve concentrically disposed about and spanning across said bearing portion and said cup and creating a void between said sleeve and the connector.

5. A connector according to claim 4 further comprising a radial expansion at an upstream end of said bearing portion and an annular rim on a downstream end of said cup, said radial expansion and said rim being cooperable to prevent longitudinal motion of said sleeve on the connector.

6. For coupling the inlet end of a tracheotomy tube inner cannula to an outlet port of an in-line catheter, a connector comprising:
   an elongated, flexible, accordion-like tubular body;
   means on a catheter entry end of said tubular body for serially coupling said body in pneumatic communication with the catheter outlet port;
   means on a catheter exit end of said tubular body for serially coupling said body in pneumatic communication with the inlet end of the tracheotomy tube inner cannula with the tracheotomy tube inner cannula inserted into said means on a catheter exit end of said tubular body; and
   means on said means on a catheter exit end of said tubular member for guiding a downstream tip of the catheter into the inlet end of the inner cannula in response to pushing the catheter at a location upstream of the catheter outlet port.

* * * * *